US009078717B2

(12) United States Patent
Griffiths et al.

(10) Patent No.: US 9,078,717 B2
(45) Date of Patent: Jul. 14, 2015

(54) SCREW WITH VARIABLE DIAMETER CANNULATION AND DRIVER

(75) Inventors: Bryan Griffiths, West Chester, PA (US); Philip Watt, West Chester, PA (US)

(73) Assignee: DePuy Synthes Products, Inc., Raynham, MA (US)

( * ) Notice: Subject to any disclaimer, the term of this patent is extended or adjusted under 35 U.S.C. 154(b) by 355 days.

(21) Appl. No.: 12/703,275

(22) Filed: Feb. 10, 2010

(65) Prior Publication Data
US 2010/0222827 A1   Sep. 2, 2010

Related U.S. Application Data

(60) Provisional application No. 61/151,353, filed on Feb. 10, 2009.

(51) Int. Cl.
*A61B 17/86* (2006.01)
*A61B 17/88* (2006.01)

(52) U.S. Cl.
CPC ............ *A61B 17/864* (2013.01); *A61B 17/8615* (2013.01); *A61B 17/8872* (2013.01); *A61B 17/8877* (2013.01); *A61B 17/8888* (2013.01)

(58) Field of Classification Search
CPC .. A61B 17/84; A61B 17/8615; A61B 17/862; A61B 17/864; A61B 17/888; A61B 17/8888
USPC .......... 606/300–321, 104; 411/407, 408, 395, 411/325, 271
See application file for complete search history.

(56) References Cited

U.S. PATENT DOCUMENTS

| 1,889,330 | A  | * | 11/1932 | Humes et al. ..................... 81/453 |
| 3,042,961 | A  | * | 7/1962  | Tieri ................................ 16/228 |
| 5,169,400 | A  |   | 12/1992 | Mühling et al. |
| 5,571,139 | A  | * | 11/1996 | Jenkins, Jr. .................... 606/232 |
| 5,902,303 | A  | * | 5/1999  | Eckhof et al. ..................... 606/60 |
| 6,168,597 | B1 | * | 1/2001  | Biedermann et al. .......... 606/310 |
| 6,454,769 | B2 | * | 9/2002  | Wagner et al. ................. 606/279 |

(Continued)

FOREIGN PATENT DOCUMENTS

| DE | 200 09 626 | 8/2000 |
| EP | 2 140 824 | 1/2010 |
| WO | WO 90/08510 | 8/1990 |

OTHER PUBLICATIONS

International Patent Application No. PCT/US2010/023703: International Search Report dated Aug. 24, 2010, 9 pages.

(Continued)

*Primary Examiner* — Matthew Lawson
*Assistant Examiner* — Si Ming Lee
(74) *Attorney, Agent, or Firm* — Baker & Hostetler LLP

(57) ABSTRACT

A bone screw driving system includes a screw having a head and a shaft extending from the head. The screw includes a stepped opening extending in the shaft that includes a first portion and a second portion having a greater cross-sectional dimension than the first portion. The bone screw driving system further includes a screw driver having a driver shaft that defines a tip configured to engage the screw head. The driver further includes a pin extending from the tip and sized to fit within the opening. The pin includes an abutment movable to a locked configuration in the second portion of the opening, wherein the abutment defines a cross-sectional dimension greater than that of the first portion of the opening.

23 Claims, 13 Drawing Sheets

(56) References Cited

U.S. PATENT DOCUMENTS

| | | | |
|---|---|---|---|
| 6,579,290 B1* | 6/2003 | Hardcastle et al. | 606/247 |
| 6,730,092 B2* | 5/2004 | Songer | 606/308 |
| 7,249,544 B2 | 7/2007 | Totsu | |
| 2003/0105468 A1 | 6/2003 | Gorek | |
| 2004/0068261 A1* | 4/2004 | Fourcault et al. | 606/67 |
| 2005/0228400 A1* | 10/2005 | Chao et al. | 606/104 |
| 2006/0025773 A1 | 2/2006 | Yevmenenko et al. | |
| 2008/0269768 A1* | 10/2008 | Schwager et al. | 606/104 |
| 2009/0187194 A1 | 7/2009 | Hamada | |
| 2009/0281580 A1* | 11/2009 | Emannuel | 606/304 |
| 2010/0069970 A1* | 3/2010 | Lewis et al. | 606/301 |

OTHER PUBLICATIONS

International Patent Application No. PCT/US2010/023703: Notification of Transmittal of the International Preliminary Report on Patentability dated May 30, 2011, 35 pages.

* cited by examiner

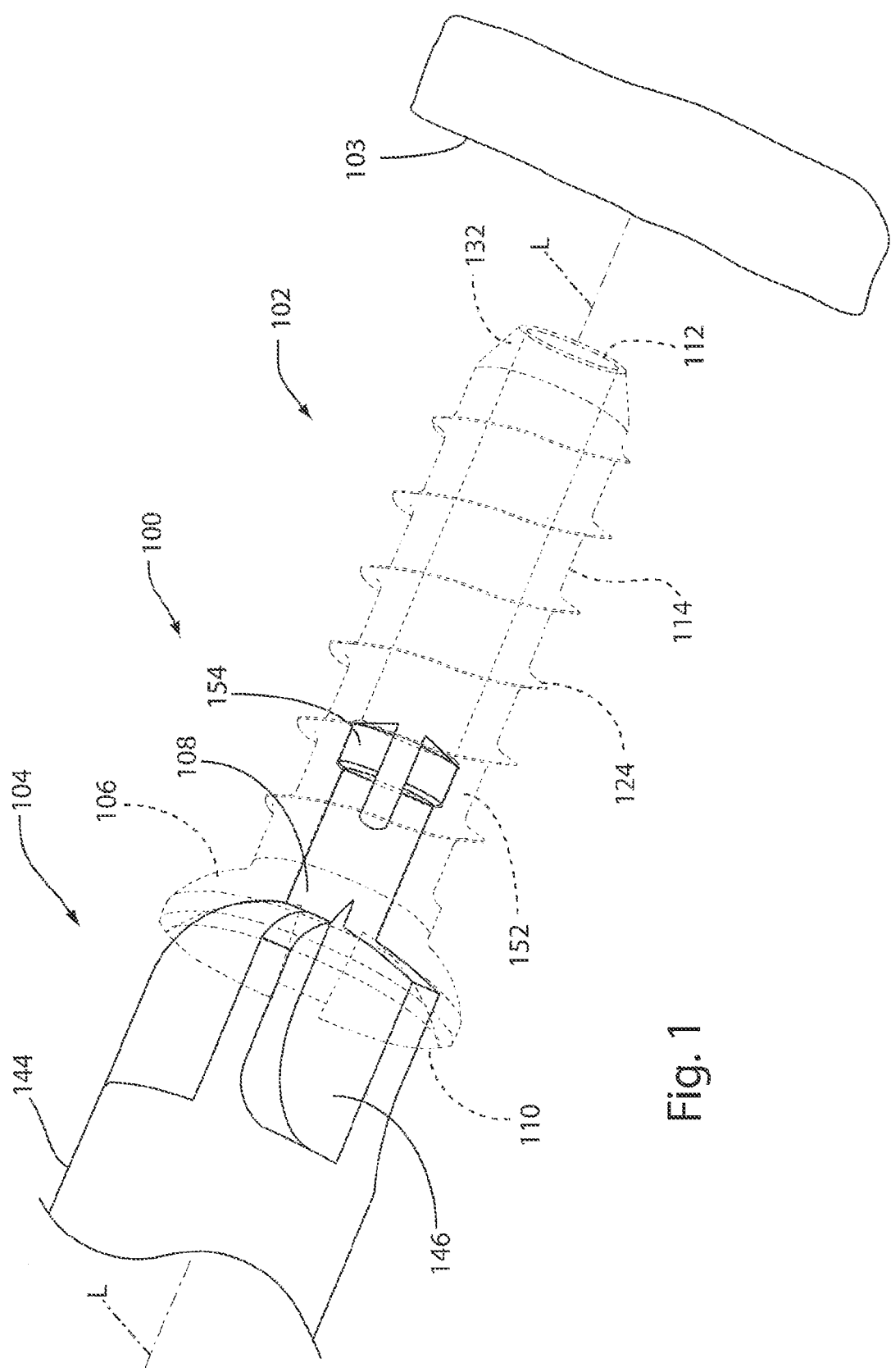

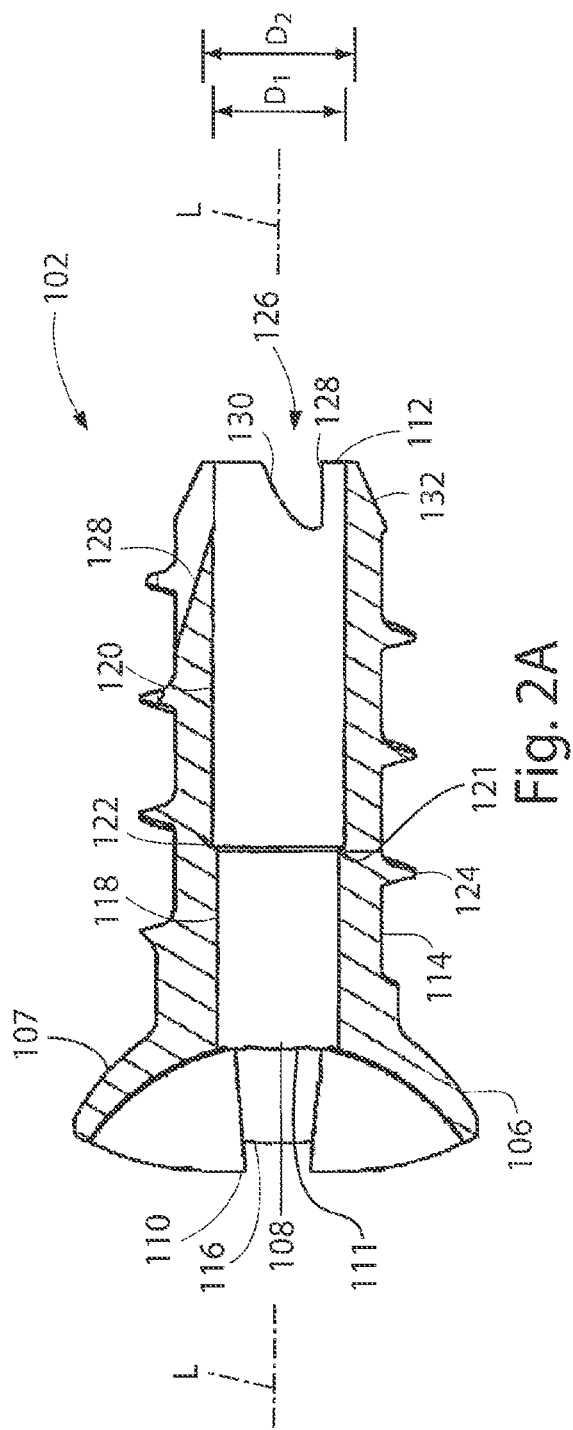

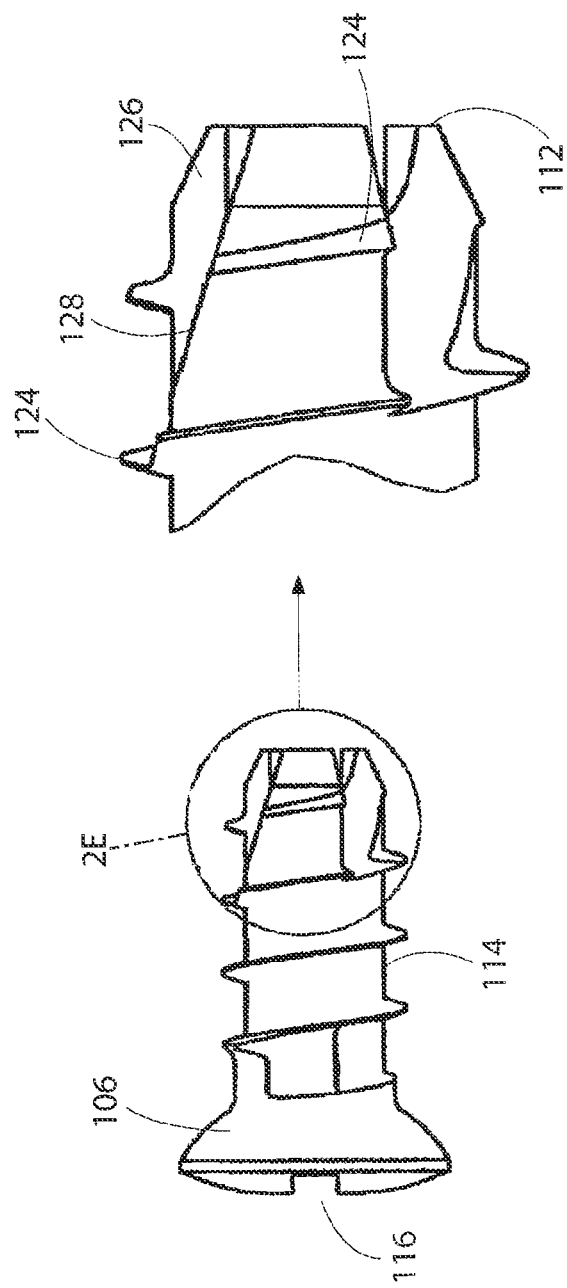

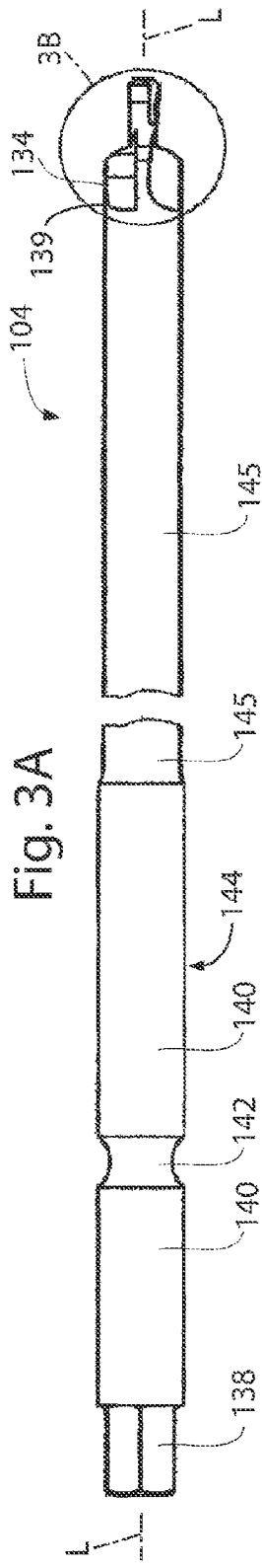
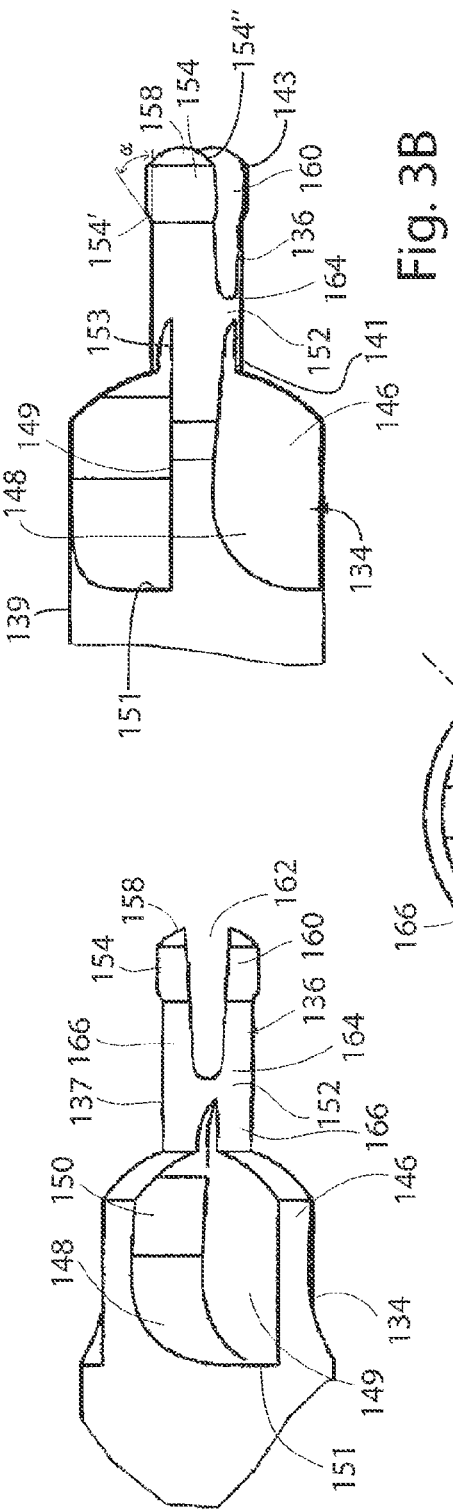
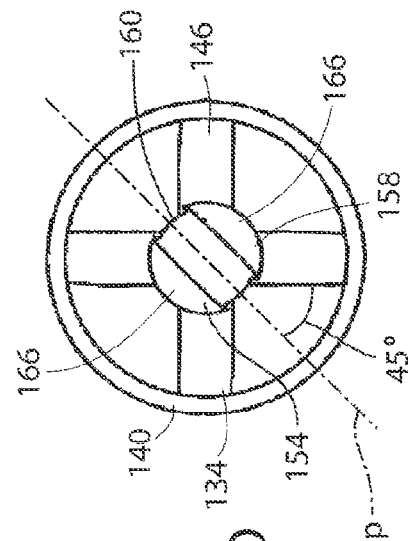

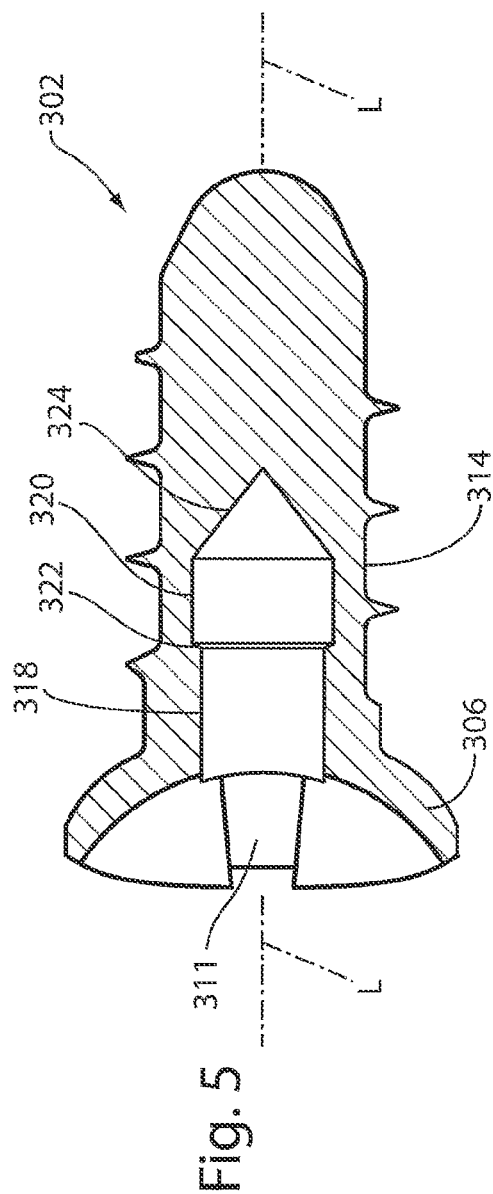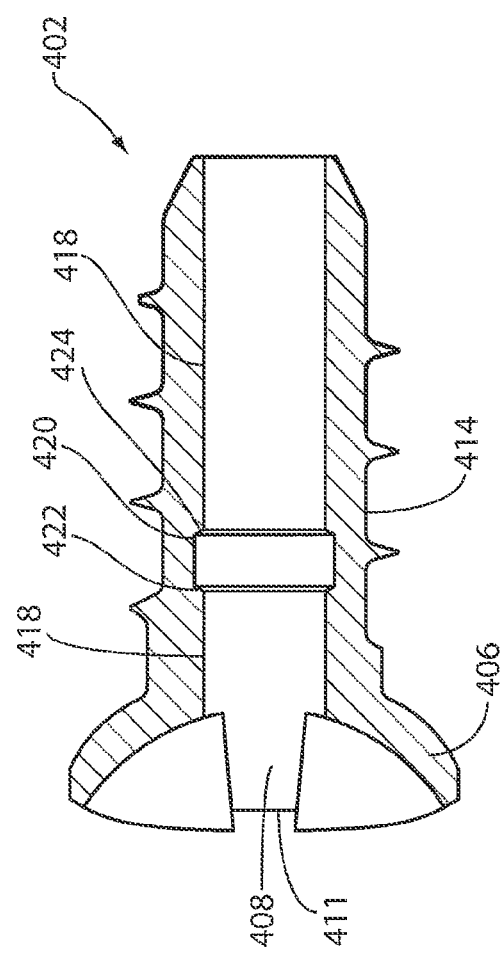

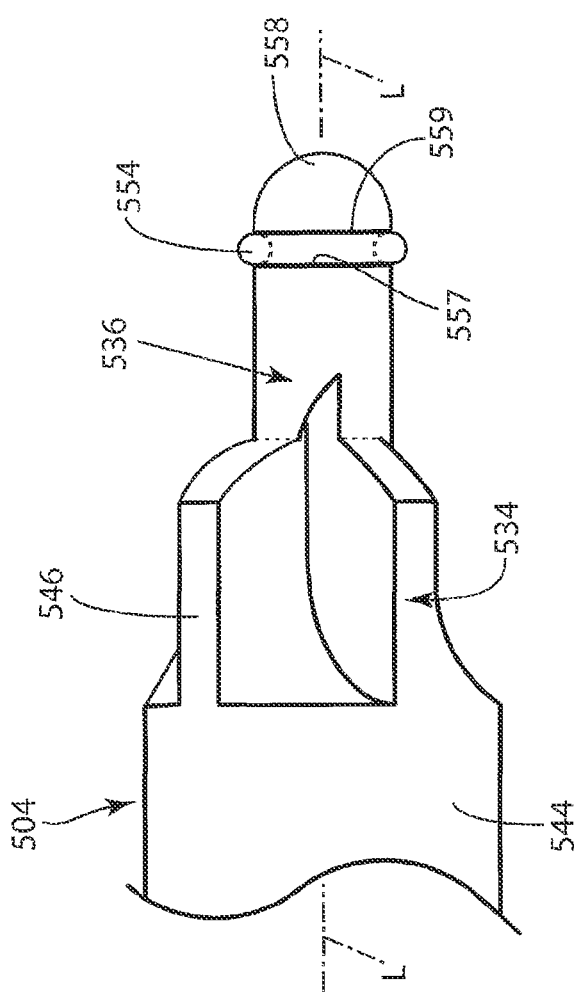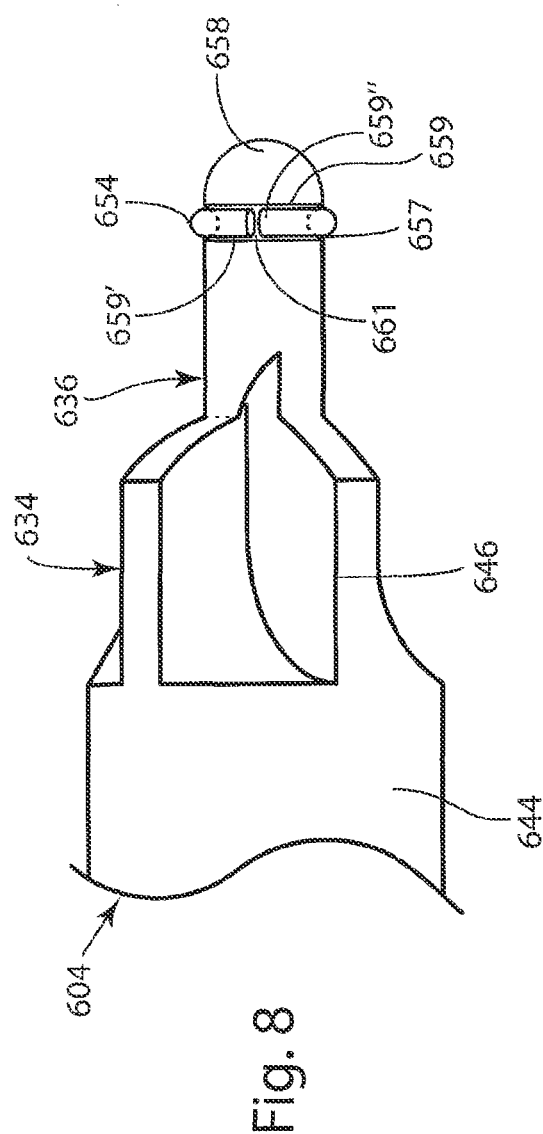

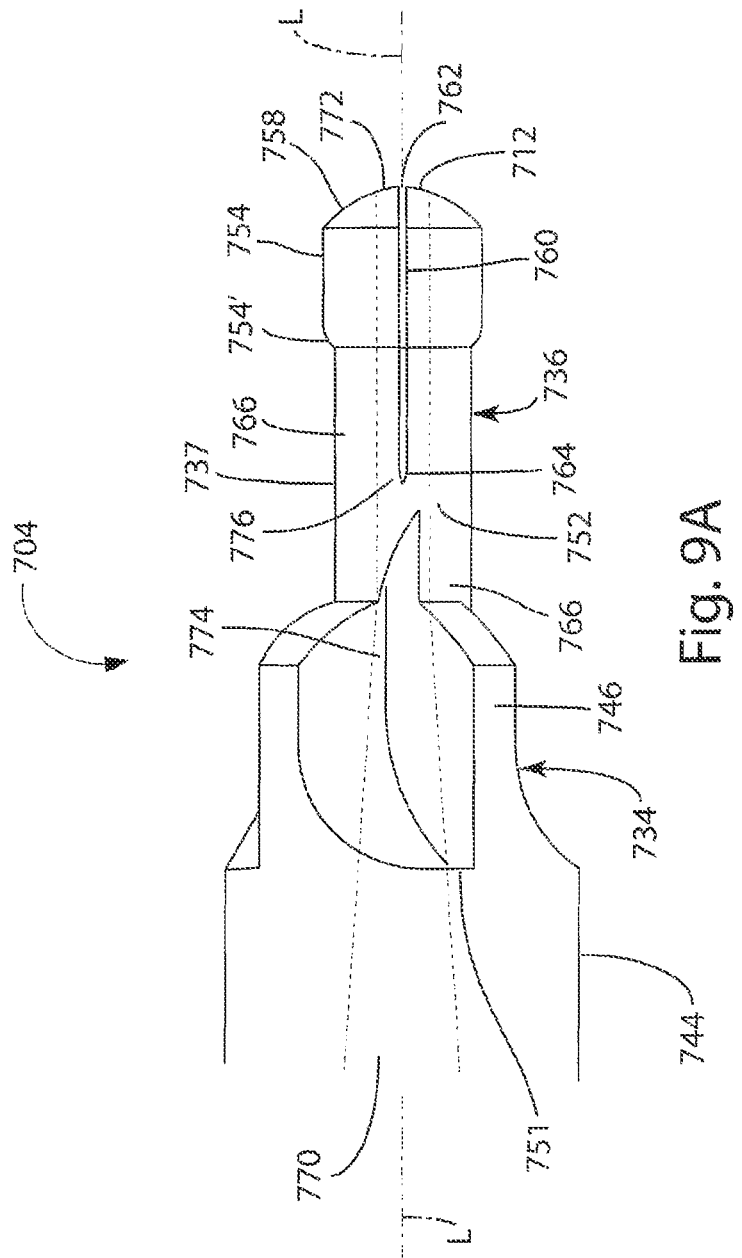

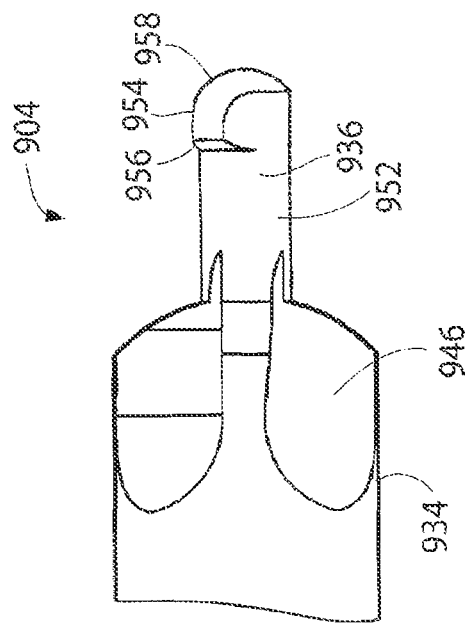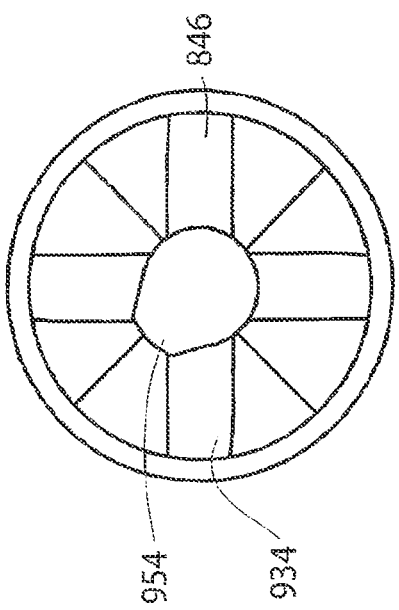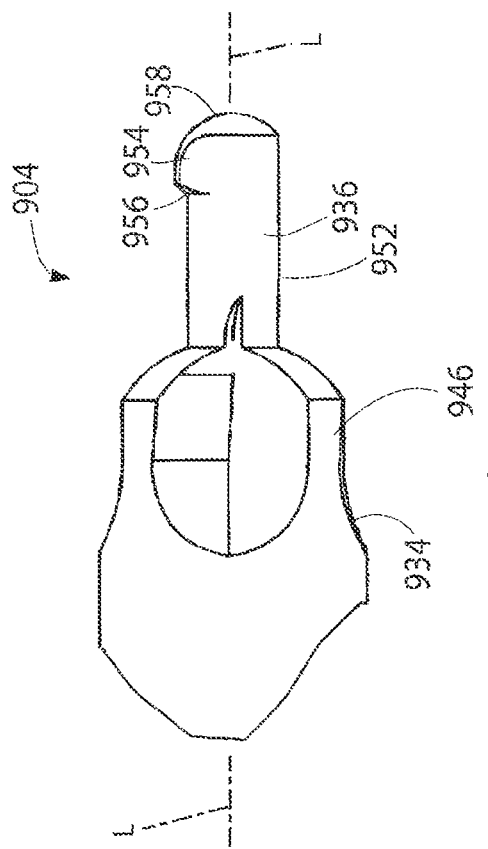

SCREW WITH VARIABLE DIAMETER CANNULATION AND DRIVER

CROSS REFERENCE TO RELATED APPLICATIONS

This application claims the benefit of U.S. provisional patent application Ser. No. 61/151,353 filed on Feb. 10, 2009, disclosure of which is hereby incorporated by reference as if set forth in its entirety herein.

BACKGROUND

Bone fixation screws for use in Cranio-Maxillofacial surgery are generally designed with small diameters and low profile heads including tool engaging structures (e.g., recesses shaped to correspond to the shape of the tool). The engagement of the tool with the bone screw permits the transfer of torque from the tool to the bone screw. In some circumstances, for instance during mandibular fixation procedures, the torque applied from the driver to the bone fixation screw occurs at angulations that can cause the driver to back out from the screw, thereby disengaging the coupling between the driver and screw. Furthermore, if the tool is not accurately aligned with the screw head, the applied torque can approach a failure level, which causes the engaging structures in the head to deform and ultimately results in failure of the coupling between the driver and the screw. The engagement between the bone screw and the driver is then compromised and a specialized surgical tool must be used to manipulate the bone screw within the body. What is therefore desired is a method and apparatus for more reliably coupling a driver tool and a bone fixation screw.

SUMMARY

In accordance with one aspect, a bone fixation screw extending along a longitudinal axis is provided. The bone fixation screw includes a screw head defining a slot configured to engage a driver and defining a proximal end of the bone fixation screw. The bone fixation screw further includes a threaded shaft extending distally from the head to a distal screw tip. The bone fixation screw defines an opening extending longitudinally through the screw head and at least into the threaded shaft. The opening defines a first portion having a first cross-sectional dimension in a direction transverse to the longitudinal axis, and a second portion disposed distal of the first portion, the second portion having a second cross-sectional dimension in a direction transverse to the longitudinal axis, wherein the second cross-sectional dimension is greater than the first cross-sectional dimension.

In accordance with another aspect, a bone fixation screw driver includes a driver shaft extending along a longitudinal axis between a proximal end and an opposing distal end. The driver shaft defines a tip at the distal end, wherein the tip is configured to engage a screw head slot. The bone fixation screw driver further includes a pin extending from the tip along the longitudinal direction. The pin includes a pin shaft that defines a cross-sectional dimension and a longitudinal length, wherein the length is at least twice cross-sectional dimension.

BRIEF DESCRIPTION OF THE DRAWINGS

The foregoing summary, as well as the following detailed description of example embodiments, are better understood when read in conjunction with the appended diagrammatic drawings. For the purpose of illustrating the invention, the drawings show embodiments that are presently preferred. The invention is not limited, however, to the specific instrumentalities disclosed in the drawings.

FIG. 1 is a perspective view of a bone driving system including a bone screw and driver constructed in accordance with one embodiment;

FIG. 2A is a partial sectional side elevation view of the bone screw of FIG. 1;

FIG. 2B is a proximal end elevation view of the bone screw illustrated in FIG. 2A;

FIG. 2C is a distal end elevation view of the bone screw illustrated in FIG. 2A;

FIG. 2D is a side elevation view of the bone screw illustrated in FIG. 2A;

FIG. 2E is an enlarged side elevation view of a portion of the bone screw illustrated in FIG. 2D;

FIG. 3A is a side elevation view of the driver illustrated in FIG. 1;

FIG. 3B is an enlarged side elevation view of the driver illustrated in FIG. 3A;

FIG. 3C is an enlarged side elevation view of the driver similar to FIG. 3B, but showing the driver rotated by 45°;

FIG. 3D is a distal end elevation view of the driver illustrated in FIG. 3A;

FIG. 5 is a sectional side elevation view of bone screw constructed in accordance with another alternative embodiment;

FIG. 6 is a sectional side elevation view of bone screw constructed in accordance with another alternative embodiment;

FIG. 7 is a side elevation view of a driver constructed in accordance with an alternative embodiment;

FIG. 8 is a side elevation view of a driver constructed in accordance with another alternative embodiment;

FIG. 9A is a side elevation view of a driver constructed in accordance with another alternative embodiment;

FIG. 11A is a side elevation view a driver constructed in accordance with another alternative embodiment;

FIG. 11B is a side elevation view of the driver illustrated in FIG. 11A, showing the driver rotated by 45°;

FIG. 11C is a distal end elevation view of the driver illustrated in FIG. 11B.

DETAILED DESCRIPTION

Figure 4A:
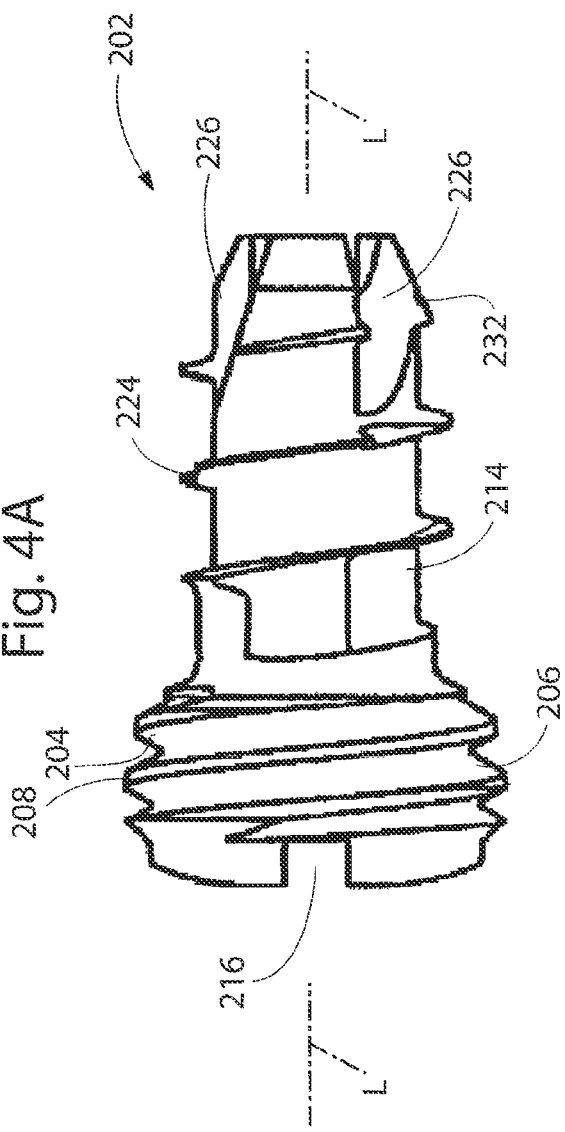
FIG. 4A is a side elevation view of a bone screw constructed in accordance with an alternative embodiment.

Methods and devices are disclosed for the insertion or removal of bone screws. For instance, bone screws and drivers are disclosed that are sized and shaped that allow the driver to engage a bone screw to selectively manipulation the bone screw while reducing the possibility that the driver will disengage from the screw with respect to conventional drivers and bone screws. The embodiments described herein may thus be employed with any of a plurality of procedures involving the insertion or removal of bone screws from a bone or bone plate as would be understood by those skilled in the art. In one embodiment, screws and drivers for use with Craniomaxillofacial ("CMF") mandible implants, as those skilled in the art will understand. Those skilled in the art will understand that, as used in this application, the term proximal refers to a direction approaching a physician or other user of the device of the present invention while the term distal refers to a direction approaching a target bone into which the bone screw is to be inserted.

Referring to FIGS. 1-2E, a bone screw driving system 100 includes a bone fixation screw driver 104 sized and shaped to engage a bone screw 102. The bone screw 102 includes a screw shaft 114 extending along a central longitudinal axis L-L, and a screw head 106 that is coupled to the proximal end of the screw shaft 114 and is sized and shaped to engage the driver 104. The screw head 106 can define any diameter as desired based on the desired end application, and in one embodiment defines an outer diameter of approximately 3.5 mm or any diameter as desired, for instance within the range of approximately 3.0 mm and 4.0 mm. The screw head 106 defines a proximal end 110 of the bone screw 102, and the shaft 114 defines a distal screw tip 132 disposed at an opposing distal end 112 of the bone screw 102. The proximal and distal ends 110 and 112 are separated along a longitudinal direction a distance as desired, for instance within the range of approximately 5.0 mm 20.0 mm. The bone screw 102 defines an opening 111 extending longitudinally through the head 106 and at least into the shaft 114. In accordance with the illustrated embodiment, the opening 111 is a cannula 108 extending through the bone screw 102, from the proximal end 110 of the screw to the distal end 112.

Referring also to FIG. 3D, the driver 104 includes a shaft 144 includes a driver tip 134 at its distal end, and a pin 136 extending distal from the driver tip 134. The tip 134 is sized and shaped to engage the head 106 of the bone screw 102, and the pin 136 is sized and shaped to be received in the opening or cannula 108, thereby increasing the stability of the screw 102 against the driver 104 during insertion or removal from a target bone 103, as will be described in more detail below.

The bone screw 102 will now be described with reference to FIGS. 1-2D. In accordance with the illustrated embodiment, the bone screw 102 is formed as a self-tapping having threads 124 protruding out from the shaft 114, which extends distally from the screw head 106. The screw 102 includes a slot 116 formed in the proximal end of the head 106 that is configured to engage the tip 134 of the driver. The slot 116 can define any width as desired (along a transverse direction, meaning transverse to the longitudinal direction). For instance, the width of the slot 116 can be within the range of 0.5 mm and 0.7 mm, for instance approximately 0.57 mm. While the slot 116 is illustrated as a crosshead or cruciform shaped-slot, the slot 116 can comprise any shape known in the art, including a flat-head slot, a hexagonal, square, or star-shaped slot, or any suitable alternatively shaped slot suitable to be engaged by a complementary shaped driver tip.

As shown in FIG. 2A, the crosshead slot 116 is open to the cannula 108 which extends along the central longitudinal axis L-L of the bone screw 102. The head 106 can have a substantially smooth outer surface 107 so as to provide a non-locking or compression bone screw 102 in accordance with one embodiment. Otherwise stated, the screw head 106 is unable to threadedly engage corresponding threads in a screw hole extending through a bone plate or other implant. In accordance with certain embodiments, bone screws are provided as locking screws having screw heads whose radially outer surfaces are threaded (see e.g., FIGS. 4A-4C).

The opening or cannula 108 can be stepped, so as to define a first portion 118 having a first cross-sectional dimension or diameter D1 that transitions to a second portion 120 having a second cross-sectional dimension or diameter D2 that is different than the first diameter. In accordance with the illustrated embodiment, the second diameter D2 is greater than the first diameter D1. The diameters D1 and D2 are substantially constant as illustrated, however it should be appreciated that they could increase or decrease along a longitudinal proximal or distal direction. It should be appreciated that the first portion 118 is disposed proximal with respect to the second portion 120 that is disposed distal to the first portion 118. Thus, in accordance with the illustrated embodiment, the first portion 118 can be referred to as a proximal portion, while the second portion 120 can be referred to as a distal portion.

It should also be appreciated that while various structure is described herein as defining diameters, the various structure described herein is not limited to being cylindrical, and thus can be said to define cross-sectional dimensions, which are in a direction transverse with respect to the longitudinal axis L-L. In accordance with certain embodiments, the cross-sectional dimensions define diameters.

The cannula includes a transition portion 121 that is disposed between the proximal portion 118 and the distal portion 120, and gradually transitions between the proximal and distal portions. The transition portion 121 can be provided as a ledge 122 that defines a beveled wall with a predetermined bevel angle (e.g., between 10° and 90°) and length as desired. In accordance with one embodiment, the first diameter D1 of the proximal portion 118 is approximately 1.05 mm, and the second diameter D2 of the distal portion 120 is approximately 1.15 mm. It is noted however that the diameter of the cannula 108 may be modified, for instance, to reflect the particular procedures to be performed, the amount of torque to be applied to the screw, the or shearing force to which the bone screw 102 is to be subjected, and other factors. The proximal portion 118 may extend into the screw 102 by a distance of approximately 1-4 mm distally from the head 106 although this length may vary with respect to a length of the bone screw 102.

The bone screw 102 may comprise a thread 124 oriented and sized in the same manner as conventional bone screws. In order to facilitate the insertion of the bone screw 102 into a target portion of bone, a distal end of the thread 124 may be tapered to the distal tip 132, which can have a reduced diameter with respect to the remained of the shaft, and can extend for example at an angle of approximately 25° with respect to the longitudinal axis L-L.

The distal end 112 of the shaft 114 may include a plurality of cutting slots 126 extending substantially proximally into the distal tip 132 as desired, as is understood by one having ordinary skill in the art. As shown in FIG. 2C, the bone screw 102 may comprise three cutting slots 126 substantially evenly disposed about a circumference of the bone screw 102. The cutting slots 126 comprise a first substantially planar cut 128 extending proximally into the shaft 114 at an angle of, for example, approximately 17° with respect to the longitudinal axis L-L. The bone screw 102 includes a second cut 130 extending back toward the distal end 112 at approximately the same angle and with a convex radius of curvature with respect to the cutting slot 126. In the exemplary embodiment shown, the cutting slots 126 intersect two adjacent turns of the thread 124. However, it should be appreciated that the cutting slots 126 may extend through any number of coils of the thread 124 as desired. The cutting slots 126 impart a sharp edge that permits bone material to be sheared by the bone screw 102 as the bone screw 102 is inserted into a target portion of bone.

Referring now to FIGS. 3A-D, the driver 104 configured to manipulate the bone screw 102 includes a shaft 144 extending centrally along the longitudinal axis L-L, and defining a proximal end 138 and an opposing distal end 139. The proximal end 138 can define any suitable shape (e.g., hexagonal) configured to non-rotatably couple to a receptacle of a screw driver body or other device. The shaft 144 includes a first section 140 and a second section 145 that is disposed distal with respect to the first section 140. The second section 145 has a second cross-sectional dimension or diameter that is different than that of the first section 140, and is less than that of the first section 140 in accordance with the illustrated embodiment, thereby allowing a push-sleeve to be inserted over the shaft 144 while also minimizing instrument obscuring of a line of vision. A portion of the shaft 144 and first diameter section 140 can be etched with a part number or label to aid in identification.

The shaft 144 defines a circumferential groove 142 extending into, but not through, the first section 140. The curved groove 142 is configured to engage a locking mechanism of the screw driver body as is understood by one having ordinary skill in the art. The driver 104 includes a screw-engaging driver tip 134 coupled to the distal end 139 of the shaft 144, and in particular at the distal end of the second section 145. The tip 134 of the driver 104 extends centrally along the longitudinal axis L-L, and is sized and shaped to engage the slot 116 of the bone screw 102. Specifically, the tip 134 includes a plurality of circumferentially evenly spaced blades 146. Each blade 146 defines a proximal end 151 coupled to the distal end 139 of the shaft 144, and an opposing distal end 153. Each blade 146 includes a first side wall 148 that is curved at the proximal end 151 from a direction substantially perpendicular to the longitudinal axis L-L to a direction extending substantially parallel to the longitudinal axis at the distal end 153. Each blade 146 further includes a second side wall 149 extending substantially parallel to the longitudinal axis L-L from the proximal end 151 to the distal end 153.

In the illustrated embodiment wherein the tip 134 includes four blades 146, each of the blades is separated from the adjacent blades 146 by approximately 90°. The blades 146 can be approximately 0.456 mm thick, or define any other thickness as desired. It should be appreciated, of course, that the tip 134 can define any shape known in the art, including a flat-head tip, a hexagonal, square, or star-shaped tip, or any suitable alternatively shaped tip suitable to engage the screw slot 116.

The driver 104 further includes a pin 136 that projects in a longitudinally outward direction from the tip 134 and in particular from the distal end 153 of the blades 146. The pin 136 extends centrally along the longitudinal axis L-L, and defines a proximal portion 141 extending out from the distal end 153 of the blades 146, and an opposing distal portion 143 which defines the distal end of the driver 104. The proximal portion 141 of the pin shaft 152 has a longitudinal length substantially equivalent to the longitudinal length of the proximal portion 118 of the cannula 108. The pin 136 can be formed by any known method including, for example, machining, forging or adjoining of two separately formed components, etc. of any sufficiently rigid material.

The pin 136 includes a pin shaft 137 having a diameter or cross-sectional dimension that is less than the diameter or cross-sectional dimension of the diver shaft 144, and slightly less than the cross-sectional dimension or diameter of the opening 111 or cannula 108. The pin shaft 137 has a longitudinal length that is at least twice the distance of its cross-sectional dimension or diameter, which provides the driver 104 with greater stability when engaging the bone screw with respect to conventional drivers. The pin 136 includes an abutment 154 extending transversely (or radially) out from the distal end 143 of the pin shaft 137. Thus, the abutment 154 has a cross-sectional dimension or diameter greater than that of the pin shaft 137, and has a longitudinal length less than that of the pin shaft 137.

The abutment 154 includes a tapered proximal end 154' that extends inward toward the pin shaft 152 along a proximal direction. In accordance with the illustrated embodiment, the tapered proximal end 154' defines an angle $\alpha$ of approximately 25° with respect to the longitudinal axis L-L. In one embodiment, the angle $\alpha$ may range from approximately 10° to approximately 90°. Alternatively, the proximal end 154 can be curved instead of tapered. The abutment defines a distal end 154" that defines a rounded tip 158 that provides an insertion guide when slidably inserting the abutment 154 past the proximal portion 118 of the cannula 108. The pin 136 further defines an opening in the form of a slot 160 extending longitudinally into the pin shaft 152, and in particular into the rounded tip 158 along a proximal direction, so as to provide a bifurcated pin 136. The slot 160 terminates at a proximal end 164 disposed in the pin shaft 152 at a location proximal with respect to the abutment 154.

The slot 160 thus defines a pair of distal pin arms 166 disposed at the distal end of the pin 136 and separated by the slot 160. Thus, the distal arms 166 are compressible from a first outer cross-sectional dimension or diameter in a first unbiased configuration to a second reduced cross-sectional dimension or diameter in its compressed configuration. The outer cross-sectional dimension or diameter of the arms 160 in their first or unbiased configuration is greater than the diameter of the proximal portion 118 of the cannula 108, and can further be greater than the diameter of the distal portion 120.

In this regard, the pin 136, and in particular the abutment 154, can be said to be compressible under a biasing force applied by the screw 102 from a first or initial configuration defining a first outer dimension, to a second configuration defining a second outer dimension that can be reduced with respect to the first outer dimension when the abutment 154 is disposed in the first or proximal portion 118, to a third locked configuration defining a third outer dimension that is greater than the second outer dimension when disposed in the second portion 120 so as to prevent the driver from being inadvertently removed from the opening or cannula 108. In accordance with one embodiment, the third outer dimension is also less than the first outer dimension. It should be appreciated that the second outer dimension can be equal to the first outer dimension, for instance as described below with reference to FIGS. 9A-C. It should further be appreciated the abutment 154 may assume different intervening configurations and corresponding dimensions between the first and third configurations depending on the configuration of the opening or cannula 108.

In accordance with the illustrated embodiment, the slot 160 defines a plane P that extends transverse to the longitudinal axis L-L in a direction that defines an approximate 45° angle with respect to planes defined by the blades 146, though the angle can be anywhere between 0° and 90° as desired. The slot 160 can be rounded its proximal end 164 as illustrated so as to provide a smooth transition between arms 166 formed on either side of the slot 160. In the illustrated embodiment, the 160 may be approximately 1.75 mm long, though it can extend any length as desired, and preferably extends to a location disposed proximal with respect to the proximal end of the abutment 154.

The slot 160 defines a width extending in a direction normal to the arms 166 that increases in a direction from the proximal end 164 to the distal end 143. In the illustrated embodiment, the width of the slot 160 can be between approximately 0.3 mm and approximately 0.5 mm. For instance the slot 160 can have a minimum width of approximately 0.3 mm at the proximal end 164, and a maximum width of approximately 0.5 mm at the distal end 143. Alternatively, the slot 160 defines a substantially uniform width of approximately 0.05 mm. to 0.75 mm. As will be described in greater detail below, the slot 160 permits radially inward flexing of the arms 166 when subjected to a radially compressive force as the abutment 154 is inserted distally past the proximal portion 118 of the cannula 108. When the abutment 154 has penetrated distally into the cannula 108 to the point at which the proximal end 154' thereof is distal of the ledge 122, the arms 166 spring radially outward to lock the pin 136 within the cannula 108.

During operation, the driver 104 is engaged with the bone screw 102, which can at the time be stored in a screw module or screw-retention housing. The driver 104 picks up the screw 102 from the screw module prior to insertion adjacent the bone plate. The pin 136 is then inserted into the cannula 108 until the abutment 154 is inserted into the proximal portion 118, which causes the arms 166 to compress toward each other, assuming a compressed configuration in which the outer cross-sectional dimension or diameter of the compressed abutment 154 is substantially equivalent to the cross-sectional dimension or diameter of the proximal portion 118 of the cannula 108.

The driver 104 may then be rotated to align the blades 146 with the respective crosshead slots 116. Once the blades 146 and the slot 116 is aligned, further distal insertion of the driver 104 into the screw causes the blades 146 to engage the crosshead slot 116, and also causes the abutment 154 to move distally from the proximal portion 118, past the ledge 122, and into the distal portion 120. Thus, the longitudinal distance or length between the proximal end 141 of the pin 136 and the abutment 154 can be less than the distance between the proximal end 110 of the bone screw 102 and the ledge 122, but greater than the distance between the proximal end of the proximal portion 118 and the ledge 122.

Once the abutment 154 is received within the distal portion 120 of the cannula 108, the abutment 154 expands to assume a locking configuration whereby the arms 166 define an outer cross-sectional dimension or diameter that is greater than that of the compressed configuration. In particular, the cross-sectional dimension or diameter of the arms 166 in the locking position can be equal to that of the original unbiased configuration, or can still be compressed in an intermediate configuration whereby the cross-sectional dimension or diameter of the arms 166 is less than that of the original configuration but greater than that of the compressed configuration.

A physician or other user of the system 100 may then manipulate the screwing device connected to the hexagonal proximal portion 138 of the driver 104 to screw or unscrew the bone screw 102 as desired. Engagement of a proximal end 154' of the abutment 154 with the ledge 122 prevents the pin 136 from being easily or inadvertently retracted from the cannula 108. In this configuration, the driver 104 is locked with respect to the bone screw 102 and is not proximally or distally movable with respect thereto.

Alternatively, the longitudinal distance or length between the proximal end 141 of the pin 136 and the abutment 154 can be greater than the distance between the proximal end 110 of the bone screw 102 and the ledge 122, such that the abutment 154 is disposed in the distal portion 120 prior to engagement of the blades 146 and the crosshead slot 116.

When it is desired to remove the driver 104 from the bone screw 102, a force can be applied to the driver 104 in a proximal direction relative to the bone screw 102 sufficient to cause the beveled proximal portion 154' of the abutment 154 to ride along the ledge 122 and compress the arms 166 toward each other to their compressed configuration, whereby the driver 104 can be removed from the bone screw 102.

When the bone screw 102 is to be inserted into a target portion of underlying bone 103, the driver 104 can be rotated in an insertion direction until a torque is applied sufficient to drive the bone screw 102 into underlying bone. Engagement of the pin 136 in the opening 111 or cannula 108 prevents inadvertent angular displacement of the driver blades 146 with respect to the slot 116, while interference between the abutment 154 and the ledge 122 prevents inadvertent removal of the driver 104 from the screw. Prevention of each advertent driver motion, both alone and in combination, prevents the shearing of the head 106 of the bone screw 102 while providing a stable connection between the driver 104 and the bone screw 102 during insertion and removal of the bone screw 102. The driver 104 can then be removed from the bone screw 102 by application of a proximally directed force to the driver 104 sufficient to apply a radially compressive force from the ledge 122 to the arms 166 via the tapered proximal end 154' of the abutment 154. This will again flex the arms 166 radially inward permitting the pin 136 to be moved out of the cannula 108 disengaging the driver 104 from the screw 102.

To remove a bone screw 102 from underlying bone using the driver 104, the driver 104 is first positioned in locked engagement with the bone screw 102 in the manner described above, and rotated in a direction opposite to an insertion direction (e.g., if the bone screw 102 was inserted by screwing in a clockwise direction, the driver 104 is rotated in a counter-clockwise direction).

It should be appreciated that the bone screw driving system 100 and methods of inserting and removing a bone screw into and from underlying bone have been described in accordance with one embodiment, and that numerous alternative embodiments are contemplated for providing enhanced securement of a driver to a bone screw. Thus, drivers and bone screws are contemplated in accordance with alternative embodiments. The alternative embodiments are intended to fall within the scope of the present invention, unless otherwise noted, but the present invention is not intended to be limited to the particular embodiments described herein, unless otherwise indicated.

Figure 4C:
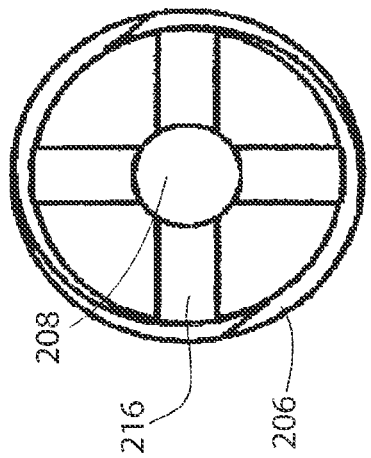
FIG. 4C is a proximal end elevation view of the bone screw illustrated in FIG. 4A.
Figure 4B:
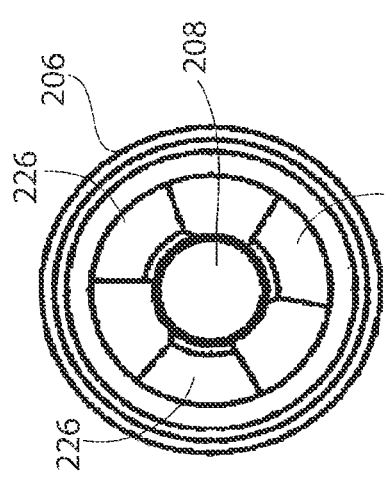
FIG. 4B is a distal end elevation view of the bone screw illustrated in FIG. 4A.

Referring now to FIGS. 4A-4C, a bone screw 202 constructed in accordance with an alternative embodiment is illustrated including reference numerals corresponding to like elements of the bone screw 102 incremented by 100 for the purposes of form and clarity. The bone screw 202 is substantially as described above with respect to the bone screw 102 with the exception that the screw head 206 includes threads 204 projecting out from the outer surface 207. The outer surface 207 is substantially cylindrical and tapers distally, and is thus configured to be lockingly engage complementary threads of a target bone plate hole. Thread 204 of the bone screw 202 can extends radially outward from the outer surface 207 so as to define an angle that can be, for instance between approximately 30° and approximately 60° relative to the longitudinal axis L-L. The threads 204 can taper distally along a direction parallel to the outer surface 207. The thread 204 terminates at a distal end of the head 206 adjacent the screw shaft 214.

The head 206 of the bone screw 202 also comprises a crosshead slot 216 to permit engagement with the tip 134 of the driver 104 in the manner described above with respect to the bone screw 102. For instance, as shown in FIG. 4C, the crosshead slot 216 opens into an opening, which in one embodiment is a cannula 208, extending longitudinally through the bone screw 202 along the central longitudinal axis L-L. The cannula 208 may also comprises a proximal portion (not shown) comprising first diameter which transitions to a second increased diameter at a distal portion (not shown), as described in greater detail with respect to FIGS. 2A-3C. The bone screw 202 can further include a plurality of cutting slots 226 extending proximally into the distal end of the shaft 214. As shown in greater detail in the distal view of FIG. 4B, the bone screw 202 may, for example, comprise three evenly circumferentially spaced cutting slots 226. The cutting slots 226 may be formed substantially as described above with respect to the cutting slots 126 of FIGS. 2A-2D. The distal end of the shaft 214 may further comprise a tapered portion 232 in which a wall of the shaft 214 tapers radially inward at a predetermined angle. The bone screw 202 may be operated in a manner substantially as described above with respect to the bone screw 102.

Referring now to FIG. 5, a bone screw 302 constructed in accordance with an alternative embodiment is illustrated including reference numerals corresponding to like elements of the bone screw 102 incremented by 200 for the purposes of form and clarity. The bone screw 302 is substantially as described above with respect to the bone screw 102 with the exception that the opening 311 does not necessarily extend entirely through the length of a bone screw 302, but rather through a predetermined portion of the bone screw. Thus, the opening 311 extends through the screw head 306 and into the shaft 314 a distance sufficient to define the first or proximal portion 318, the transition portion or ledge 322, and the second distal portion 320 of different (for instance greater as illustrated) cross-sectional dimension or diameter with respect to that of the proximal portion 318 in the manner described above. The expanded distal portion 320 allows the abutment 154 to expand therein, thereby locking the driver 104 to the screw 302. In this regard, it should be appreciated that the term "locked" does not refer to a state where the driver 104 is incapable of being removed from the screw, but rather that the driver 104 and screw 302 engage so as to prevent unintentional removal of the driver 104 from the screw, absent a force sufficient to compress the arms 166 in the manner described above. The distal portion 320 of the opening 311 can define a substantially conical tip 324 or any suitable shape.

Referring now to FIG. 6, a bone screw 402 constructed in accordance with an alternative embodiment is illustrated including reference numerals corresponding to like elements of the bone screw 102 incremented by 300 for the purposes of form and clarity. The bone screw 402 is constructed substantially as described above with respect to the bone screw 102 with the exception that the bone screw 402 includes a second portion provided as a groove 420 projecting outwardly from the cannula 408 into the screw shaft 114. Thus, the cannula 408 defines a first portion 418 having a first cross-sectional dimension or diameter as described above that is disposed both proximal and distal with respect to the second portion 420. The second portion or groove 420 defines a diameter having a cross-sectional dimension or diameter different than (for instance greater than, as illustrated) the first cross-sectional dimension or diameter of the first portion 418 in the manner described above.

However, the groove 420 does not extend to the terminal end of the cannula 408 as described with respect to the bone screw 102. Rather, the groove 420 terminates at a location proximal with respect to the distal end of the cannula 408 so as to define a third portion 418 having a cross-sectional dimension or diameter less than the second diameter of the groove 420. In the illustrated embodiment, the first and third portions 418 define the same cross-sectional dimension or diameter. The second portion or groove 420 is adjoined to the first portions 418 via respective transition portions or ledges 422 and 424 that are tapered between the larger diameter of the groove 420 and the smaller diameters of the first and second portions 418.

The expanded diameter groove 420 is disposed at a predetermined distance from the head 406 so as to be aligned with the abutment 154 of the driver 104 when the blades 146 engage the slot 116. In this regard, the distance from the proximal end of the cannula 418 to the tapered wall or ledge 422 is substantially equal, or slightly less than, to the distance from the proximal end of the pin 106 to the proximal end 154' of the abutment 154. The groove 420 has a longitudinal length equal to or greater than the longitudinal length of the abutment 154 formed at a distal end of the pin 136 to, such that the abutment 154 to radially expand therein into locking engagement with the screw 402.

Referring now to FIG. 7, a driver 504 constructed in accordance with an alternative embodiment is illustrated including reference numerals corresponding to like elements of the driver 104 incremented by 400 for the purposes of form and clarity. The driver 504 includes an abutment separated 554 longitudinally from a distal end 508 of the pin 536 by a predetermined distance along the longitudinal axis L-L. Specifically, the abutment 554 comprises a compressible o-ring 559 retained in a groove 557 that projects radially into the pin 536, and thereby locks the ring 559 on the pin 536 with respect to longitudinal movement relative to the pin 536. The ring 559 may be made from any suitably compressible structure or material. For instance, the ring 559 can be made from an elastomeric material, and/or can be provided as a spring insert disposed a predetermined distance proximally of the distal end 508.

The ring 559 is coupled to the pin 536 so that, when the driver 504 is inserted into, for example, the cannula 418 the bone screw 402, the ring 559 expands into the increased diameter portion of the second portion or groove 420, thereby locking the driver 504 to the screw 402 in the manner described above. It should be appreciated, of course, that the driver 504 can be used in combination with any of the other bone screws described herein, such that the ring 559 is can become locked in the second portion of the opening or cannula having an increased diameter relative to the first portion of the opening or cannula in the manner described above. It should further be appreciated that, depending on the material properties of the ring 559, the ring 559 is movable circumferentially within the groove 557. Accordingly, once the ring 559 has been inserted into the first portion of an opening or cannula of a bone screw so that the ring 559 is compressed, the pin 536, and thus the driver 504, is rotatable with respect to the ring 559, thereby allowing a user to more easily align the blades 546 with the slot(s) of the screw head.

It should be appreciated that, as illustrated Alternatively, the tip 534 and pin 536 can be provided as a unitary structure devoid of a slot such as the slot 160 of the pin 136. Alternatively, the pin 536 can be bifurcated by a slot as described above with respect to the pin 13. It should be appreciated that the tip 534 of the driver can be otherwise constructed substantially as described above with respect to the tip 134 of the driver 104. That is, the tip 510 includes a plurality of blades 512 formed in a crosshead shape.

Referring now to FIG. 8, a driver 604 constructed in accordance with an alternative embodiment is illustrated including reference numerals corresponding to like elements of the driver 504 incremented by 100 for the purposes of form and clarity. In particular, the abutment 654 is provided as a compressible ring 609 disposed in a groove 657 extending into the pin 636 in the manner described above with respect to the driver 504. However, the ring 659 is a split ring that defines a gap 661 extending therethrough that separates the ring 659 into first and second ring segments 659' and 659" that are separated at one end by the gap 661.

The split ring 659 may be formed of a substantially rigid material and is positioned along a length of the pin 636 so that, when the pin 636 is inserted into a screw such as, for example, the screw 402, to a desired position, the ring 659 is positioned within the increased diameter groove 420 of the cannula 408 with a proximal edge thereof engaging the proximal ledge 422 of the groove 420. Furthermore, the ring 659 is movable circumferentially within the groove 657. Accordingly, once the ring 659 has been inserted into the first portion of an opening or cannula of a bone screw so that the ring 659 is compressed, the pin 636, and thus the driver 604, is rotatable with respect to the ring 659, thereby allowing a user to more easily align the blades 646 with the slot(s) of the screw head.

When the ring 659 is subjected to a radially compressive force, for instance when the ring 659 is disposed in the first portion of a screw opening or cannula, such as first portion 418, the split ring 659 is flattened against and around the outer surface of the pin 636 reducing the profile of the pin 636 and permitting the pin 636 to be advanced into the cannula 408 until the split ring 659 enters the groove 420 and expands radially under its natural bias to lock the driver 604 to the screw 402 in the same manner described above.

The gap 661 is formed with a size sufficient to permit insertion of the split ring 659 past a proximal portion of a cannula (not shown) which comprises a diameter smaller than a diameter of the unbiased split ring 659. Specifically, as the split ring 659 of the pin 636 is inserted into the proximal portion of the cannula, the split ring 659 is forced to a compressed configuration, whereby the distance of the gap 661 between the adjacent segments 659' and 659" is reduced, as the segments approach each other. A diameter of this constricted split ring 659 is then substantially equivalent to a diameter of the first portion 418 of the cannula 408 in the compressed configuration so as to permit a slidable insertion of the pin 636 through the first portion 418 and into the second portion 420. Once the split ring 659 has been advanced into the groove 420 (or other second portion of the screw opening or cannula), the natural bias of the split ring 659 pushes the segments 659' and 659" away from one another radially expanding the diameter of the split ring 659 to a locked configuration as described above.

Figure 9B:
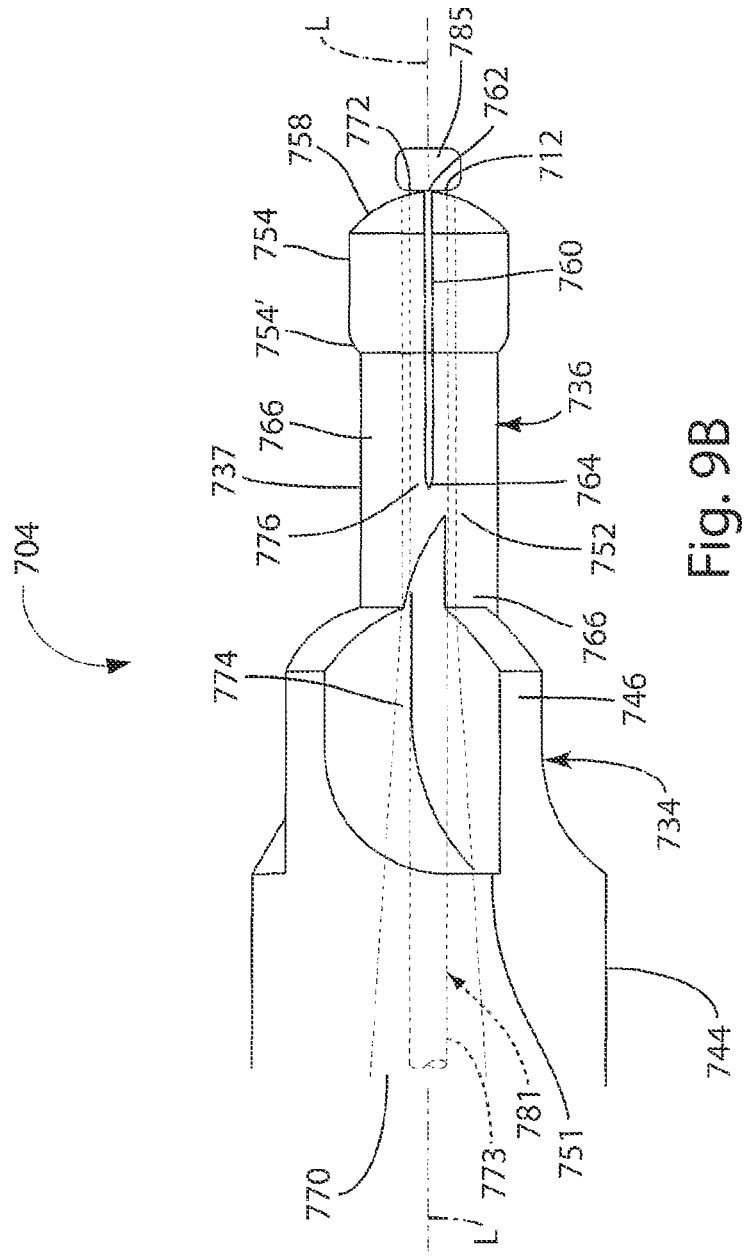
FIG. 9B is a side elevation view of the driver as illustrated in FIG. 9A, including an expansion member constructed in accordance with one embodiment.
Figure 9C:
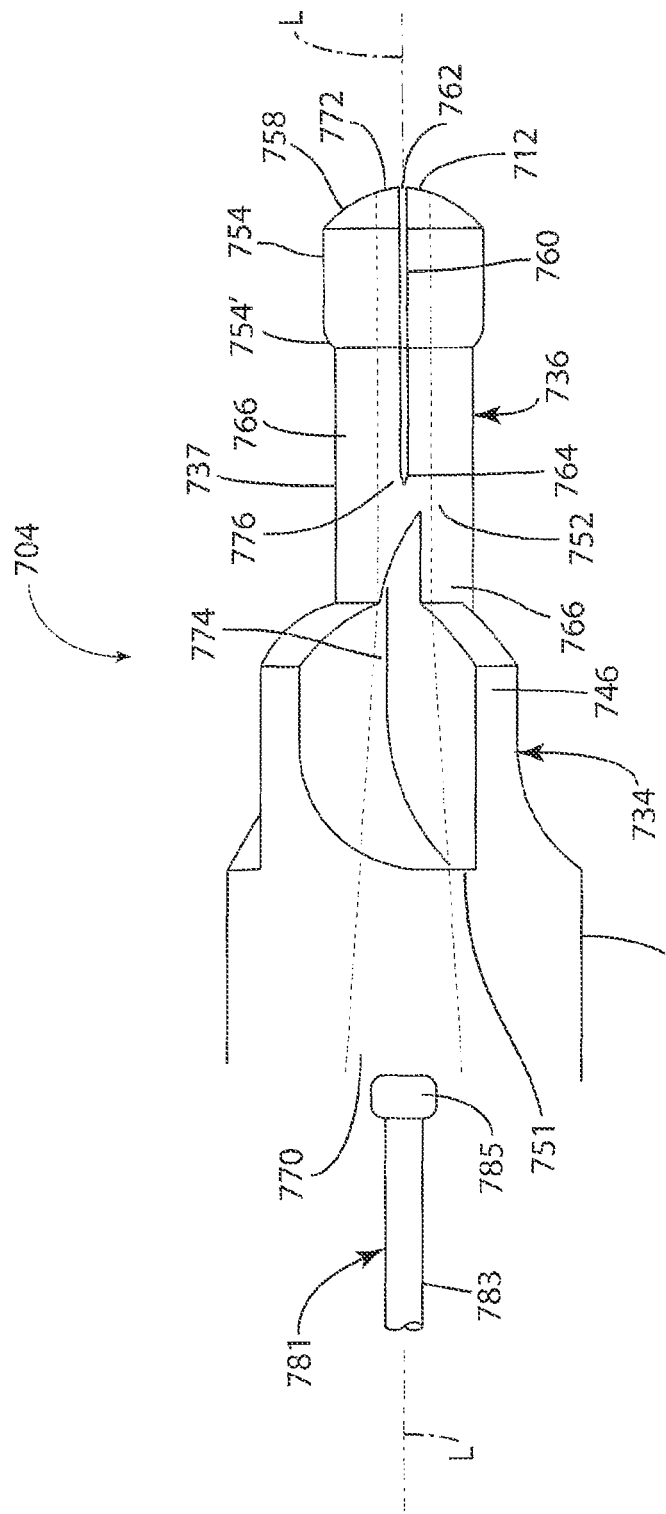
FIG. 9C is a side elevation view of the driver as illustrated in FIG. 9A, including an expansion member constructed in accordance with another embodiment.

Referring now to FIGS. 9A-C, a driver 704 constructed in accordance with an alternative embodiment is illustrated including reference numerals corresponding to like elements of the driver 104 incremented by 600 for the purposes of form and clarity. In particular, the driver is constructed substantially as described above with respect to the driver 104, with the exception that a lumen 770 extends longitudinally through the driver pin 736, tip 734, and shaft 744. The driver 704 includes an expansion pin assembly 781 configured to be received in the lumen 770.

The driver tip 734 is constructed substantially as described above with respect to driver 134, with the exceptions of the dimensions described herein. For instance, the tip 734 defines a plurality of blades 746 substantially evenly disposed about a circumference thereof. A pin 736 projects from the tip 734 and distally past the distal ends of the blades 746. The pin 736 includes a pin shaft 752 extending to an abutment 754 at a distal end thereof, wherein a diameter of the abutment is greater than that of the pin shaft 752.

In the illustrated embodiment, a diameter of the abutment 754, in an non-expanded state, is slightly smaller than an inner diameter of the proximal portion 118 of the opening 111 or cannula 108 of the bone screw 102 (or any of the bone screws as described herein). The pin shaft 752 has a longitudinal length that is substantially equal to the longitudinal length of the first portion of the opening or cannula 108. A distal end of the abutment 754 comprises a rounded tip 758 to aid in the slidable removal of the abutment 754 from a bone screw after a designated procedure has been completed.

The driver 702 further includes a slot 760 extending longitudinally into the pin 736 from an open distal end 762 of the slot 760 to a proximal end 764 of the slot 760, thereby bifurcating the slot 760 into opposing flexible arms 766. A width of the slot 760 remains substantially constant from the proximal end 764 to the distal end 762. The slot 760 permits the arms 766 to flex radially outward when subjected to a radially outward biasing force applied by the expansion pin assembly 781 as it travels through the lumen 770.

As illustrated in FIG. 9B, the expansion pin assembly 781 includes an expansion shaft 783 and an expansion pin 785 coupled to the distal end of the shaft 783. The expansion pin 785 has a cross-sectional dimension or diameter that is greater than the thickness of the slot 760. Accordingly, as the pin 785 travels through the slot 760, the pin 785 provides a force that biases the arms 766 outward in a direction away from each other. As illustrated in FIG. 9B, the expansion shaft 783 has a diameter or cross-sectional dimension less than that of the lumen 770 and slot 760. Accordingly, as illustrated in the shaft 783 can extend longitudinally through the driver 704, and can be slidable within the driver 704.

The expansion pin 785 can be a substantially cylindrical or alternatively shaped member with a diameter greater than at least a portion 776 of the lumen 770 within the pin 736 (i.e., when the arms 766 are in the non-expanded state). The lumen 770 extends longitudinally through the driver 704, and defines a distal end 772 disposed at a distal end 712 of the driver 704.

Thus, as illustrated in FIG. 9B, the expansion pin 785 can be initially disposed external to the driver 704 and positioned adjacent the distal end 712 of the driver 704. The expansion shaft 783 can extend longitudinally in a proximal direction from the expansion pin 785, through the lumen 770, and can extend out the proximal end of the driver 704. A pulling force can then be applied to the expansion shaft 783 that draws the expansion pin 785 into a portion 776 of the lumen 770 at a location aligned with the arms 766, whereby the expansion pin 785 has a greater cross-sectional dimension than the lumen portion 776. As a result, the expansion pin 785 applies a radially expansive force to the arms 766.

Alternatively, as illustrated in FIG. 9C, the expansion pin 785 can be initially disposed internal to the driver 704 and positioned adjacent the arms 766. The expansion shaft 783 can extend longitudinally in a proximal direction from the expansion pin 785. A pushing force can then be applied to the expansion shaft 783 that pushes the expansion pin 785 into a portion 776 of the lumen 770 that is aligned with the arms 766, whereby the expansion pin 785 has a greater cross-sectional dimension than the lumen portion 776. As a result, the expansion pin 785 applies a radially expansive force to the arms 766.

The arms 766 are biased so that, when not subjected to the radially expansive force, they contract radially inward to a first or non-expanded state in which an outer diameter of the abutment 754 is slightly smaller than the inner diameter of the proximal portion 118 of the cannula 108 to permit the abutment 754 to pass distally therethrough. In this regard, it should be appreciated that the abutment 754 can define an outer dimension in their second configuration (i.e., when disposed in side the cannula 108) that is equal to their outer dimension in the first configuration (i.e., before inserted into the cannula 108). After the pin 736 has been advanced into the cannula 108 so that the abutment 754 is received within the second portion 120, the expansion pin 785 is inserted through the portion 776 of the lumen 770, thereby biasing the arms 766 outward and expanding abutment 754 to a third locked configuration having a third cross-sectional dimension that is greater than the second configuration, so as to lock the pin 736 within the second portion 120 of the cannula 108.

During operation, the driver 704 is engaged with a bone screw (such as bone screw 102) in the manner described above. The pin 736 is then inserted into the opening or cannula 108 in the first and second non-expanded configurations until the abutment 754 has been advanced into the distal portion 120. Because the cross-sectional dimension of the abutment 754 is less than that of the first and second portions 118 and 120 of the opening or cannula 108 when in the first and second configurations, the driver 704 can be easily rotated to align the blades 746 to engage respective slots of the crosshead slot 116. The expansion pin 785 is then inserted into the portion 776 of the lumen 770, which causes the pin 785 to bias the abutment 754 to the locked configuration, whereby the abutment 754 defines a cross-sectional dimension or diameter greater than that of the first portion 118, thereby locking the driver 704 in the cannula 108 and preventing the pin 736 from being inadvertently withdrawn from the cannula 108. The bone screw 102 may then be placed through a bone plate and driven into or out of the bone as desired by rotating the driver 704. When it is desired to disengage the driver 704 from the screw 102, the expansion pin 785 is further drawn or pushed through the driver 704 and removed from the driver 704, which causes the arms 766 to return to the non-extended configuration.

Figure 10B:
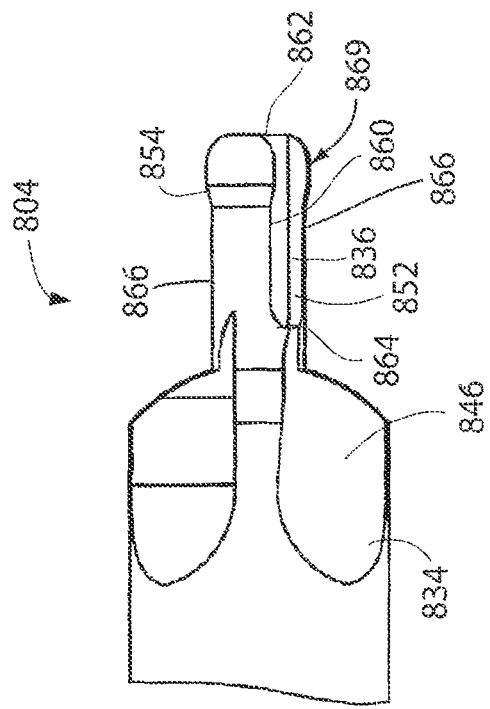
FIG. 10B is a side elevation view of the driver illustrated in FIG. 10A, showing the driver rotated by 45°.
Figure 10C:
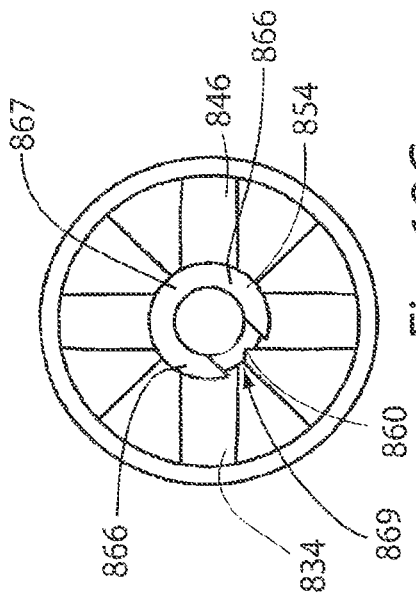
FIG. 10C is a distal end elevation view of the driver illustrated in FIG. 10B.
Figure 10A:
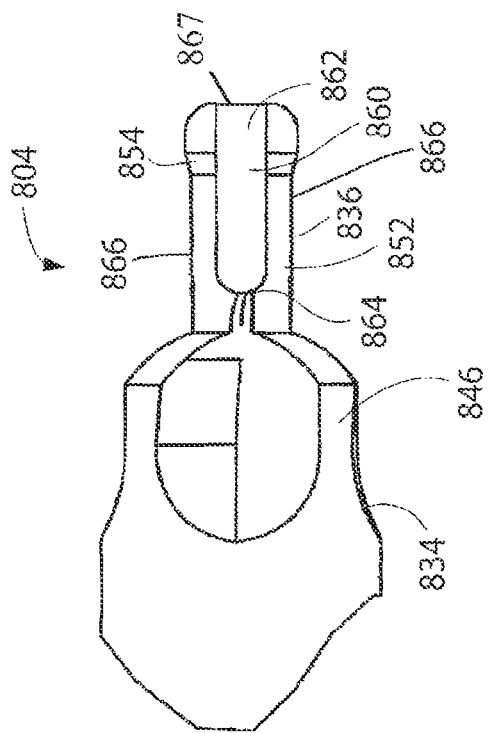
FIG. 10A is a side elevation view a driver constructed in accordance with another alternative embodiment.

Referring now to FIGS. 10A-C, a driver 804 constructed in accordance with an alternative embodiment is illustrated including reference numerals corresponding to like elements of the driver 104 incremented by 700 for the purposes of form and clarity. The driver 804 is substantially constructed as described above with respect to the driver 104, except that the slot 860 extends transversely into the pin shaft 852, but not through the pin shaft 852. Accordingly, the pin 836 defines a pair of arms 866 separated at an open transverse end 869, and a hinge 867 connecting the opposing outer transverse ends of the arms 866, such that the arms 866 define a substantially C-shaped cross sectional shape. As a result, the arms can expand and contract about the hinge 867 to iterate the abutment 854 between the first, second, and third configurations as described above. In accordance with an alternative embodiment, the driver 804 can include a lumen such as the lumen 770 illustrated in FIGS. 9A-9C configured to receive an expansion pin assembly, such as the expansion pin assembly 781 that causes the abutment 854 to iterate between the first, second, and third configurations.

Referring now to FIGS. 11A-C, a driver 904 constructed in accordance with an alternative embodiment is illustrated including reference numerals corresponding to like elements of the driver 104 incremented by 800 for the purposes of form and clarity. The driver 904 is substantially constructed as described above with respect to the driver 104, except that the pin 936 is illustrated as a solid, unitary structure that is devoid of a slot, such as slot 160. Furthermore, the abutment 954 extends transversely (or radially) out in only one direction from the pin 936, as opposing to two opposing directions as illustrated in FIGS. 3A-D. The abutment 954 is formed as a extension formed on a side of the pin shaft 952 comprising a tapered wall 956 at the proximal end of the abutment 954. The tapered wall 956 extends transversely inward toward the longitudinal axis L-L along a proximal direction. The pin 936 further includes a substantially rounded wall 958 at the distal end of the abutment 954 that adjoins with the distal end 958 of the pin shaft 952.

The driver 904 can be used in combination with a bone screw, such as the bone screw 102 described above with reference to FIGS. 2A-2C. For instance, the pin 936 can be inserted into the first portion 118 of the bone screw 102 along the longitudinal axis L-L of the opening or cannula 108, or at a predetermined angle relative to the longitudinal axis L-L of the opening or cannula 108 such that the abutment 954 defines a leading end with respect to the opposing surface of the pin 936 that is devoid of the abutment 954. The 952 can be flexible, such that the pin 936 can be inserted at an angle or along the longitudinal axis L-L, such that the abutment 954 to easily translate distally past the proximal portion 118 even though the cross-sectional dimension of the pin 936 through the abutment 954 is greater than that of the first portion 918. Once the abutment 954 moves into the distal portion 120, the abutment 954 assumes the locked configuration in the second portion 120 of the opening or cannula 108.

Figure 12:
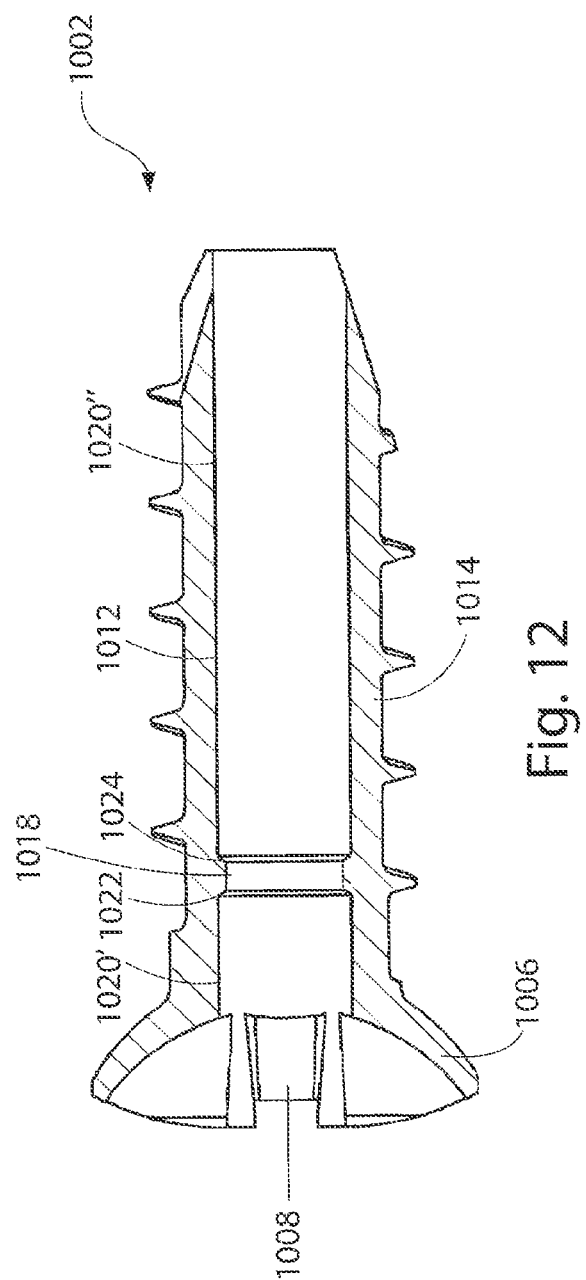
FIG. 12 is a sectional side elevation view of a bone screw constructed in accordance with another alternative embodiment.

Referring now to FIG. 12, a bone screw 1002 constructed in accordance with an alternative embodiment is illustrated including reference numerals corresponding to like elements of the screw incremented by 900 for the purposes of form and clarity. The screw 1002 is substantially constructed as described above with respect to the screw 102, except that the opening or cannulation 1008 defines a pair of second portions 1020' and 1020" disposed proximally and distally, respectively, with respect to a middle first portion 1018. The first portion 1018 can extend any longitudinal length as desired. As described above, the first portion 1018 defines a cross-sectional dimension or diameter that is less than that of the second portions 1020' and 1020". In this regard, it should be appreciated that the first portion 1018 defines a rib extending into the opening or cannula 1008 from the screw shaft 1014.

In particular, the cross-sectional dimension of the proximal second portion 1020' can be greater than that of an abutment, such as abutment 154, when the abutment is in its first configuration. As a result, the driver pin 136 can be inserted into the proximal second portion 1020', and the driver 104 can subsequently be rotated so as to align the blades 146 with the slot 1008 formed in the screw head 1006. Further distal longitudinal movement of the driver 104 relative to the bone screw 1002 causes the abutment 154 to translate into the first portion 1018 of the opening or cannula 108, thereby compressing the abutment 154 to its second or compressed configuration. Further distal longitudinal movement of the driver 104 relative to the bone screw 1002 causes the abutment 154 to translate into the distal second portion 1020" which can have a cross-section or diameter greater than that of the first portion 1018, and greater, less than, or equal to that of the proximal second portion 1020'. The abutment 154 thus expands in the distal second portion 1020" with respect to its compressed configuration in the first portion 1018, thereby interfering with the first portion 1018 with respect to forces that might otherwise unintentionally remove the driver 104 from the bone screw 102.

It will be appreciated that a kit can be provided that includes at least one bone screw of the type described herein, such as a plurality of bone screws. The plurality of bone screws can be constructed in accordance with one or more, up to all, of the embodiments described herein, or in accordance with the same embodiment. The screws can be provided in different shapes and sizes, for instance having screw shafts of various lengths and diameters. The kit can also include at least one bone screw driver of the type described herein, such as a plurality of drivers constructed in accordance with one or more than one, up to all, embodiments described herein.

It will be apparent to those skilled in the art that various modifications and variations may be made in the structure and the methodology of the present invention, without departing from the spirit or scope of the invention. For instance, the structures, features, and methods associated with the embodiments described above can be integrated into any of the other embodiments described above, unless otherwise noted. Thus, it is intended that the present invention cover modifications and variations of the invention provided, for instance as defined by the appended claims.

What is claimed is:

1. A bone fixation screw extending along a longitudinal axis, the bone fixation screw comprising:
   a screw head defining a slot configured to engage a driver, the slot defining a slot cross-sectional dimension in a direction transverse to the longitudinal axis, the screw head further defining a proximal end of the bone fixation screw; and
   a threaded shaft that defines a distal screw tip that is distal to the screw head, the distal screw tip defining a distal end of the bone fixation screw; and the bone fixation screw defining an opening extending longitudinally through the screw head and at least into the threaded shaft, wherein the slot extends from the proximal end and opens directly into a first portion of the opening having a first cross-sectional dimension in a direction transverse to the longitudinal axis, a second portion of the opening having a second cross-sectional dimension in a direction transverse to the longitudinal axis is disposed distal of the first portion, and a transition portion tapers radially outward from the first portion to the second portion, wherein the threaded shaft completely encircles the transition portion along a direction parallel to the longitudinal axis, and wherein the second cross-sectional dimension is greater than the first cross-sectional dimension, and the slot cross-sectional dimension is greater than the first cross-sectional dimension, the second portion is sized to receive a driver abutment that is inserted distally through the first portion into the second portion, and the first cross-sectional dimension is less than a cross-sectional dimension of the driver abutment when the driver abutment is disposed in the second portion.

2. The bone fixation screw as recited in claim 1, wherein the opening comprises a cannulation that extends longitudinally through the shaft.

3. The bone fixation screw as recited in claim 1, wherein the second portion extends to the distal end of the threaded shaft.

4. The bone fixation screw as recited in claim 3, wherein the first portion extends from the screw head.

5. The bone fixation screw as recited in claim 1, wherein the second portion is a distal second portion that is disposed distal with respect to the first portion, the bone fixation screw further comprising a proximal second portion that is disposed proximal with respect to the first portion, such that the proximal and distal second portions each define a cross-sectional dimension greater than that of the first portion.

6. The bone fixation screw as recited in claim 1, wherein the cross-sectional dimensions comprise diameters.

7. The bone fixation screw as recited in claim 1, wherein the screw head is threaded.

8. The bone fixation screw as recited in claim 1, wherein the slot cross-sectional dimension is measured such that the slot cross-sectional dimension crosses the opening.

9. The bone fixation screw as recited in claim 1, wherein the screw head defines an outer diameter and the slot cross-sectional dimension is measured along the outer diameter.

10. The bone fixation screw as recited in claim 1, wherein the threaded shaft completely encircles the entire first portion in the longitudinal direction.

11. The bone fixation screw as recited in claim 1, wherein the threaded shaft completely encircles the second portion as the second portion extends from the transition portion in the longitudinal direction.

12. The bone fixation screw as recited in claim 1, wherein the distal end of the bone fixation screw further comprises a plurality of cutting slots extending substantially proximally into the distal screw tip, wherein the plurality of cutting slots defines a sharp edge configured to shear bone material as the bone fixation screw is inserted into a target portion of bone.

13. A kit comprising:
   at least one bone screw that is elongate along a longitudinal axis that defines a center of the bone screw, the at least one bone screw including:
      a screw head defining a slot configured to engage a driver and defining a proximal2 end of the at least one bone screw; and
      a threaded shaft that defines a distal screw tip that is distal to the screw head, the at least one bone screw defining an opening extending longitudinally through the screw head and at least into the threaded shaft, wherein the slot extends from the proximal end of the opening and defines a screw head portion that longitudinally extends from a proximal end of the screw head to a distal end of the screw head, the screw head portion opens directly into a first portion extending from the screw head portion, the first portion having a first cross-sectional dimension in a direction transverse to the longitudinal axis, a second portion having a second cross-sectional dimension in a direction transverse to the longitudinal axis is disposed distal of the first portion, and a transition portion tapers radially outward from the first portion to the second portion toward the threaded shaft in the direction from the proximal end to the distal end of the bone screw, wherein the second cross-sectional dimension is greater than the first cross-sectional dimension and the first cross-sectional dimension is less than a cross-sectional dimension of the slot; and
   at least one bone screw driver including:
      a driver shaft extending along a longitudinal axis between a proximal end and an opposing distal end, the driver shaft defining a tip at the distal end, wherein the tip is configured to engage with the screw head slot of one of the at least one bone screw such that the driver shaft is rotationally coupled to the one of the at least one bone screw; and
      a pin extending from the tip along the longitudinal direction, the pin including a pin shaft and an abutment, the pin shaft positioned between the tip and the abutment, the pin configured to assume a locked configuration inside the second portion when the abutment is compressed as it is inserted through the first portion and then the abutment expands as the abutment is inserted into the second portion, wherein the abutment defines a cross-sectional dimension greater than the first cross-sectional dimension when the abutment is inserted into the second portion.

14. The kit as recited in claim 13, wherein the abutment is compressible.

15. The kit as recited in claim 14, wherein the pin defines a slot extending into the distal end of the pin shaft along a proximal direction so as to define a pair of spaced pin arms.

16. The kit as recited in claim 15, wherein the slot extends through the pin shaft and the abutment along a direction transverse to the longitudinal direction.

17. The kit as recited in claim 15, wherein the slot extends into, but not through, the pin shaft and the abutment along a direction transverse to the longitudinal direction, such that the arms are connected at one transverse end by a hinge.

18. The kit as recited in claim 14, wherein the abutment comprises a ring disposed in a groove formed in the pin shaft.

19. The kit as recited in claim 18, wherein the ring is a split ring.

20. The kit as recited in claim 13, wherein the screw head defines a head outer diameter in a direction transverse to the longitudinal axis and threaded shaft defines a shaft outer diameter in a direction transverse to the longitudinal axis, and no portion of the shaft outer diameter is greater than the head outer diameter.

21. The kit as recited in claim 20, wherein the head outer diameter is greatest at the proximal end.

22. The kit as recited in claim 21, wherein the head outer diameter gradually tapers along the longitudinal direction towards the threaded shaft.

23. The kit as recited in claim 13, wherein the distal end of the at least one bone screw further comprises a plurality of cutting slots extending substantially proximally into the distal screw tip, wherein the plurality of cutting slots defines a sharp edge configured to shear bone material as the at least one bone screw is inserted into a target portion of bone.

* * * * *